United States Patent
Fukuyama

(10) Patent No.: US 9,513,223 B2
(45) Date of Patent: Dec. 6, 2016

(54) SCANNING OBSERVATION APPARATUS

(71) Applicant: OLYMPUS CORPORATION, Tokyo (JP)

(72) Inventor: Hiroya Fukuyama, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/829,983

(22) Filed: Aug. 19, 2015

(65) Prior Publication Data

US 2015/0355094 A1 Dec. 10, 2015

Related U.S. Application Data

(63) Continuation of application No. PCT/JP2014/054427, filed on Feb. 25, 2014.

(30) Foreign Application Priority Data

Feb. 25, 2013 (JP) ................. 2013-034591

(51) Int. Cl.
*G01J 1/58* (2006.01)
*G01T 1/10* (2006.01)
(Continued)

(52) U.S. Cl.
CPC ............ *G01N 21/6456* (2013.01); *G02B 21/06* (2013.01); *G02B 21/365* (2013.01); *G01N 2201/10* (2013.01); *G01N 2201/121* (2013.01)

(58) Field of Classification Search
CPC ..................... G01N 21/6456; G01N 2201/121; G01N 2202/10; G02B 21/06; G02B 21/365
(Continued)

(56) References Cited

U.S. PATENT DOCUMENTS

2004/0061048 A1 4/2004 Vasic et al.
2005/0224721 A1 10/2005 Aoki
(Continued)

FOREIGN PATENT DOCUMENTS

JP 2001-272346 A 10/2001
JP 2005-300310 A 10/2005
(Continued)

OTHER PUBLICATIONS

International Search Report dated May 20, 2014 issued in PCT/JP2014/054427.

*Primary Examiner* — Yara B Green
*Assistant Examiner* — Abra Fein
(74) *Attorney, Agent, or Firm* — Scully, Scott, Murphy & Presser, P.C.

(57) ABSTRACT

A high-resolution fluorescence image in which an afterimage is suppressed is obtained, even when a fluorescence detection interval is shortened. Provided is a scanning observation apparatus including a scanning unit that spatially scans pulsed excitation light emitted from a light source at prescribed time intervals on a specimen; a fluorescence detecting unit that detects fluorescence generated by exciting a fluorescent substance inside the specimen with the excitation light scanned by the scanning unit, in synchronization with the emission of the excitation light; and a fluorescence correcting unit that subtracts, from a fluorescence intensity detected by the fluorescence detecting unit, an afterimage fluorescence component calculated on the basis of time-sequential fluorescence detected by the fluorescence detecting unit prior thereto, at each scanning position, to correct the fluorescence intensity at the scanning position.

4 Claims, 5 Drawing Sheets

(51) Int. Cl.
*G01N 21/64* (2006.01)
*G02B 21/06* (2006.01)
*G02B 21/36* (2006.01)

(58) Field of Classification Search
USPC ..................................................... 250/458.1
See application file for complete search history.

(56) References Cited

U.S. PATENT DOCUMENTS

2009/0045353 A1    2/2009  Alexeevich et al.
2009/0078886 A1*  3/2009  Schutzmann .......... G07D 7/122
                                                                      250/459.1
2011/0320174 A1  12/2011  Ragan et al.

FOREIGN PATENT DOCUMENTS

JP          2008-541128 A    11/2008
WO    WO 2011/052248 A1    5/2011

\* cited by examiner

SCANNING OBSERVATION APPARATUS

CROSS REFERENCE TO RELATED APPLICATIONS

This is a continuation of International Application PCT/JP2014/054427, with an international filing date of Feb. 25, 2014, which is hereby incorporated by reference herein in its entirety. This application claims the benefit of Japanese Patent Application No. 2013-034591, the contents of which are incorporated herein by reference.

TECHNICAL FIELD

The present invention relates to a scanning observation apparatus.

BACKGROUND ART

In the related art, there is a known scanning observation apparatus that obtains a fluorescence image by scanning pulsed excitation light emitted from a light source on a specimen, detecting fluorescence generated in the specimen, and associating the detected fluorescence intensity with the scanning position of the excitation light (for example, see Patent Literature 1).

In such a scanning observation apparatus, in order to obtain a high-resolution fluorescence image, it is necessary to shorten the irradiation interval of the pulsed excitation light and the detection interval of the fluorescence.

CITATION LIST

Patent Literature

{PTL 1}
PCT International Publication No. WO2011/052248

SUMMARY OF INVENTION

One aspect of the present invention is a scanning observation apparatus including a scanning unit that spatially scans pulsed excitation light emitted from a light source at prescribed time intervals on a specimen; a fluorescence detecting unit that detects fluorescence generated by exciting a fluorescent substance inside the specimen with the excitation light scanned by the scanning unit, in synchronization with the emission of the excitation light; and a fluorescence correcting unit that subtracts, from a fluorescence intensity detected by the fluorescence detecting unit, an afterimage fluorescence component calculated on the basis of time-sequential fluorescence detected by the fluorescence detecting unit prior thereto, at each scanning position, to correct the fluorescence intensity at the scanning position.

DESCRIPTION OF EMBODIMENT

A scanning observation apparatus 1 according to an embodiment of the present invention will be described below with reference to the drawings.

Figure 1:
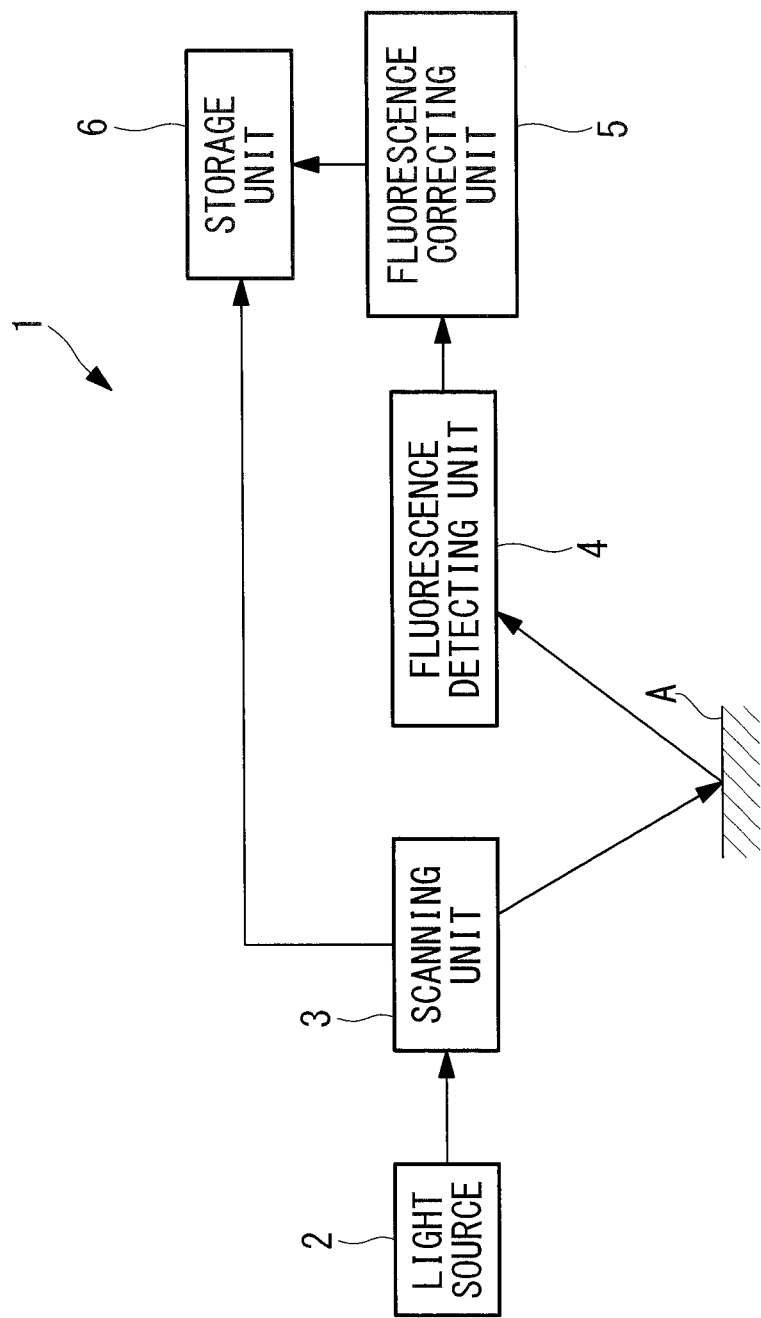
FIG. 1 is a block diagram showing a scanning observation apparatus according to an embodiment of the present invention.

As shown in FIG. 1, the scanning observation apparatus 1 according to this embodiment includes a scanning unit 3 that spatially scans excitation light emitted from a light source 2 on a specimen A, a fluorescence detecting unit 4 that detects fluorescence generated in the specimen A by irradiating the specimen A with the excitation light by means of the scanning unit 3, a fluorescence correcting unit 5 that corrects the fluorescence intensity detected by the fluorescence detecting unit 4, and a storage unit 6 that stores the fluorescence intensity corrected by the fluorescence correcting unit 5 and the scanning position scanned by the scanning unit 3 on the specimen A in association with each other.

The light source 2 is configured so as to emit pulsed excitation light with prescribed time intervals therebetween.

The scanning unit 3 includes an optical system (not illustrated) that guides the light from the light source 2 and a scanning means (not illustrated), such as proximity galvanometer mirrors, that two-dimensionally scans the light guided by the optical system on the specimen A.

The fluorescence detecting unit 4 includes a detection optical system (not illustrated) that collects the fluorescence generated in the specimen A, in synchronization with the irradiation of the specimen A with the excitation light emitted from the light source 2, and a photodetector (not illustrated), such as a photomultiplier tube, that detects the fluorescence collected by the detection optical system. Accordingly, the fluorescence detecting unit 4 can obtain a time-sequential sequence of fluorescence signals separated by the same time intervals as those of the excitation light, at a timing that is synchronized with the emission timing of the excitation light from the light source 2.

The fluorescence correcting unit 5 is configured to perform correction, for one of all the fluorescence signals in the obtained time-sequential sequence of fluorescence signals, for subtracting an afterimage fluorescence component based on the fluorescence signal obtained before that fluorescence signal.

Figure 2A:
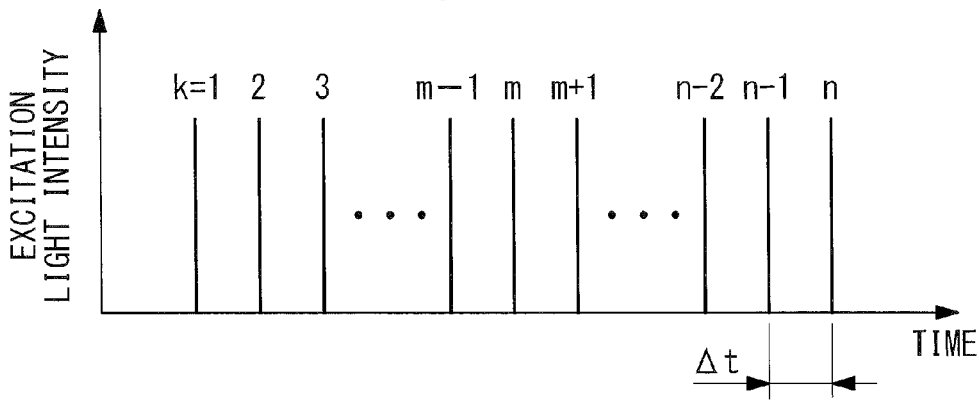
FIG. 2A is a diagram showing temporal changes in excitation light emitted from a light source in the scanning observation apparatus in FIG. 1.
Figure 2B:
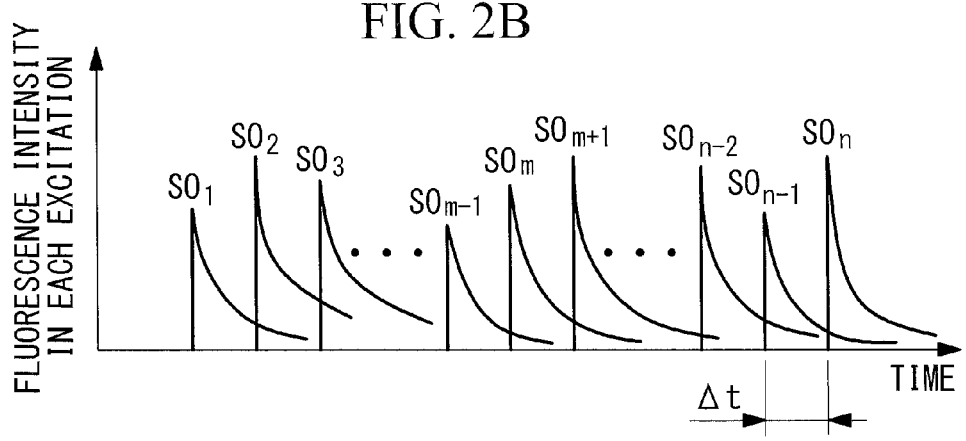
FIG. 2B is a diagram showing temporal changes in fluorescence generated in each excitation in the scanning observation apparatus in FIG. 1.
Figure 2C:
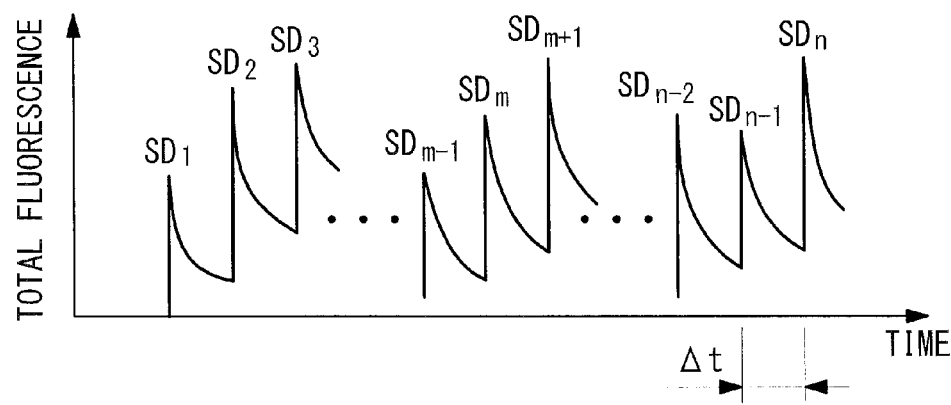
FIG. 2C is a diagram showing temporal changes in the fluorescence actually detected in the scanning observation apparatus in FIG. 1.

In other words, as shown in FIG. 2A, when the specimen A is irradiated with pulses of excitation light at prescribed time intervals, immediately after excitation light irradiation, as shown in FIG. 2B, fluorescence is generated by exciting a fluorescent substance inside the specimen A. However, the fluorescence generated in each excitation light irradiation continues to be generated in such a manner as to exhibit a tail up to a position that overlaps with the fluorescence generated subsequently, according to the fluorescence lifetime thereof, and therefore, as shown in FIG. 2C, the intensity of the fluorescence actually detected by the photodetector contains a plurality of overlapping fluorescences and thus becomes higher than the fluorescence generated by irradiation with the excitation light at each time.

Figure 3:
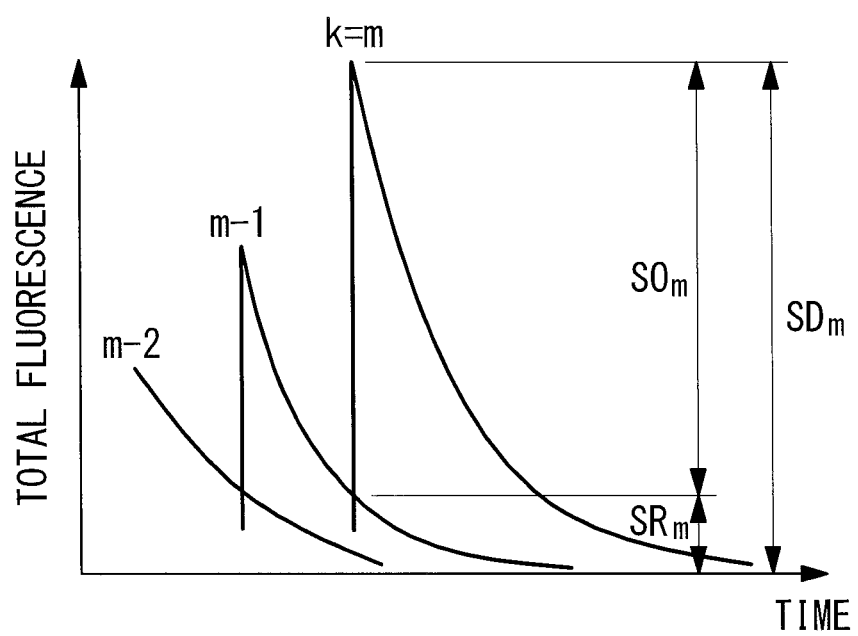
FIG. 3 is a diagram for explaining the relationship of each fluorescence component in FIG. 2C.

As shown in FIG. 3, when the fluorescence signal actually detected at time m is $SD_m$, the fluorescence signal generated by irradiation with the excitation light at time m is $SO_m$, and the fluorescence signal that is generated by irradiation with the excitation light earlier than time m and that persists until time m (persistent fluorescence component) is $SR_m$, the following relationship holds:

$$SO_m = SD_m - SR_m$$

Because the persistent fluorescence component $SR_m$ is determined based on the intensities of the plurality of preceding fluorescence signals and the fluorescence lifetime of the fluorescent dye, when the above relationship is rearranged, the relationship shown below is established.

Specifically, the detected fluorescence signal and the corrected fluorescence signal have the following relationship.

$$S_D = L \cdot S_O$$

$$S_D = \begin{pmatrix} SD_1 \\ SD_2 \\ SD_3 \\ \vdots \\ SD_n \end{pmatrix} \quad \{\text{MATH 4}\}$$

$$L = \begin{pmatrix} l_{11} & l_{12} & l_{13} & \cdots & l_{1n} \\ l_{21} & l_{22} & l_{23} & \cdots & l_{2n} \\ l_{31} & l_{32} & l_{33} & \cdots & l_{3n} \\ \vdots & \vdots & \vdots & & \vdots \\ l_{n1} & l_{n2} & l_{n3} & \cdots & l_{nn} \end{pmatrix}$$

$$S_O = \begin{pmatrix} SO_1 \\ SO_2 \\ SO_3 \\ \vdots \\ SO_n \end{pmatrix}$$

Here, $S_O$ is the corrected fluorescence intensity, $SO_m$ is the m-th corrected fluorescence intensity, $S_D$ is the detected fluorescence intensity, $SD_m$ is the m-th detected fluorescence intensity, $\Delta t$ is the time interval of the excitation light, $T_m$ is the fluorescence lifetime of the fluorescent dye corresponding to the m-th detection, L is a fluorescence lifetime matrix, $$l_{ij} = 0 \, (i < j), \text{ and}$$

$$l_{ij} = \exp(((j-i) \cdot \Delta t)/T_j) \, (i \geq j). \tag{1}$$

Here, the features of the fluorescence lifetime matrix L are discussed.

The above relationship shows that the persistent fluorescence component is based on the past fluorescence intensities and the fluorescence lifetime, and from the relationship in Eq. (1), the value of the determinant for the fluorescence lifetime matrix L is not zero, and thus the matrix L is regular. Therefore, since an inverse matrix $L^{-1}$ for matrix L exists, and a unique solution $S_O$ exists, we have $$S_O = L^{-1} \cdot S_D.$$

Accordingly, the fluorescence intensity detected in the fluorescence detecting unit 4 is finely corrected in the fluorescence correcting unit 5, and thus it is possible to obtain the fluorescence signal generated by irradiation with the excitation light at each time. In other words, with the scanning observation apparatus according to this embodiment, an advantage is afforded in that it is possible to obtain a high-resolution fluorescence image in which an afterimage is suppressed, even when the fluorescence detection interval is shortened.

In this case, this embodiment can be applied also to cases in which the fluorescence lifetime of the fluorescent substance present in the specimen A is not spatially uniform.

In cases where the fluorescence lifetime of the fluorescent substance present in the specimen A is spatially uniform, the above fluorescence lifetime matrix L can be simplified. Namely:

$$SO_m = SD_m - SR_m,$$

$$SR_m = \exp(-\Delta t/T) \cdot SD_{m-1},$$

where $SO_m$ is the m-th corrected fluorescence intensity, $SD_m$ is the m-th detected fluorescence intensity, $SR_m$ is the m-th afterimage fluorescence component, $\Delta t$ is the time interval of the excitation light, and T is the fluorescence lifetime of the fluorescent dye.

This shows that the persistent fluorescence component contained in the fluorescence signal detected at a certain time can be defined based on the fluorescence signal detected immediately prior thereto. In this case, a fluorescence image can be obtained more simply and more precisely than in the case with the above-described embodiment.

This embodiment has been described in terms of an example in which the fluorescence is sequentially scanned in a single viewing field; instead of this, however, the present invention may be applied to a scanning observation apparatus of the division raster scanning type in which a single viewing field is divided into a plurality of divided viewing fields, and for each irradiation with pulsed excitation light one time, the excitation light is scanned in the plurality of divided viewing fields while switching the divided viewing fields in a prescribed order.

Figure 4:
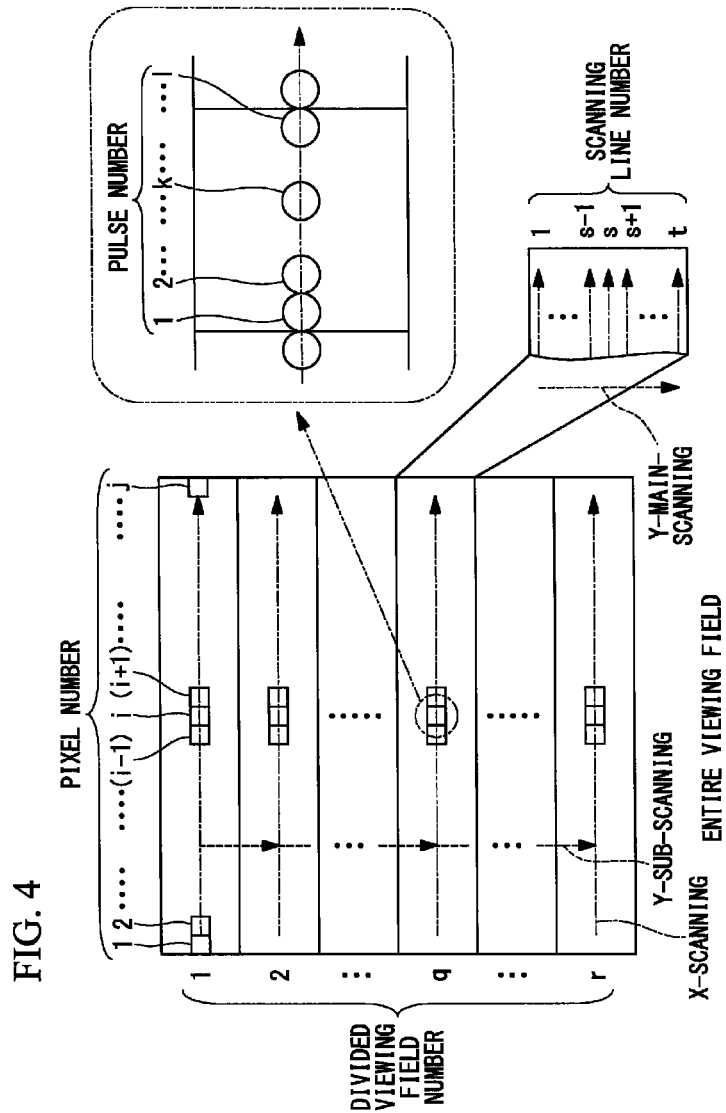
FIG. 4 is a diagram showing the general relationship of the pulses, pixels, entire viewing field, divided viewing fields, and scanning lines according to a modification of the scanning observation apparatus in FIG. 1.

FIG. 4 is a diagram for explaining scanning of the excitation light in the division raster scanning method.

In the example shown in FIG. 4, a single entire viewing field is divided into r divided viewing fields (indicated by divided viewing field numbers), and when scanning each divided viewing field in t scanning lines (indicated by scanning line numbers), for each irradiation with pulsed excitation light one time, the divided viewing fields are switched in a prescribed order (for example, in an order according to the divided viewing field number) and the excitation light is radiated. In addition, each scanning line includes j pixels (indicated by pixel numbers), and each pixel is irradiated with l pulses of excitation light (indicated by pulse numbers), and fluorescence detection is synchronously performed each time. In FIG. 4, the direction in which pixels are arrayed along the scanning lines is called the X-scan direction, the direction in which the scanning lines are switched in each divided viewing field is called the Y-main-scan direction, and the direction in which the divided viewing fields are switched is called the Y-sub-scan direction.

In other words, the entire viewing field is formed of r divided viewing fields, each divided viewing field includes t scanning lines, each scanning line includes j pixels, and each pixel includes l detected fluorescence signals. Therefore, detection of the k-th fluorescence in the i-th pixel in the s-th scanning line in each divided viewing field is completed by performing pulsed excitation light irradiation r times.

In addition, detection of the fluorescence of the i-th pixel in the s-th scanning line in each divided viewing field is completed by performing pulsed excitation light irradiation rl times, and the pixel serving as the irradiation target is switched.

Furthermore, detection of the fluorescences in the s-th scanning line in each divided viewing field is completed by performing pulsed excitation light irradiation rlj times, and the scanning line serving as the irradiation target is switched.

Thus, detection of the fluorescences in the entire viewing field is completed by performing pulsed excitation light irradiation rljt times.

In such a scanning observation apparatus, the corrected fluorescence intensity of the i-th pixel in the q-th divided viewing field can be calculated by the following equation.

{MATH 5}

$$SO_{iq} = \sum_{k=1}^{l} SO_{ikq} \quad (2)$$

$$\begin{cases} = \sum_{k=1}^{l} (SD_{ikq} - \exp(-\Delta t/T) \cdot SD_{ik(q-1)}) & (2 \leq q \leq r) \\ = \sum_{k=1}^{l} SD_{ik1} - \exp(-\Delta t/T) \cdot \left( SD_{(i-1)lr} + \sum_{k=1}^{l-1} SD_{ikr} \right) & (q=1) \end{cases} \quad (3)$$

Here, l is the number of detections of the fluorescences constituting each pixel, r is the total number of divided viewing fields, $SO_{iq}$ is the corrected fluorescence intensity of the i-th pixel in the q-th divided viewing field, $SO_{ikq}$ is the corrected fluorescence intensity the due to the k-th pulsed excitation light irradiation in the i-th pixel in the q-th divided viewing field, $SD_{ikq}$ is the detected fluorescence intensity due to the k-th pulsed excitation light irradiation in the i-th pixel in the q-th divided viewing field, $SD_{ikl}$ is the detected fluorescence intensity due to the k-th pulsed excitation light irradiation in the i-th pixel in the first (initial) divided viewing field, and $SD_{(i-1)lr}$ is the detected fluorescence intensity due to the l-th (final) pulsed excitation light irradiation in the (i−1)-th pixel in the r-th (final) divided viewing field.

Equation (2) in Math 5 shows that, with the condition 2≤q≤r, the corrected fluorescence intensity $SO_{iq}$ of the i-th pixel in the q-th divided viewing field is calculated using all of the detected fluorescence intensities $SD_{ikq}$ (1≤k≤l) in the same pixel and all of the detected fluorescence intensities $SD_{ik(q-1)}$ (1≤k≤l) in the i-th pixel in the (q−1)-th divided viewing field.

Also, Equation (3) in Math 5 shows that, assuming q=1, the corrected fluorescence intensity $SO_{i1}$ of the i-th pixel in the first divided viewing field is calculated using all of the detected fluorescence intensities $SD_{ikl}$ (1≤k≤l) in the same pixel, the final detected fluorescence intensity $SD_{(i-1)lr}$ in the (i−1)-th pixel in the r-th divided viewing field, and all of the detected fluorescence intensities $SD_{ikr}$ (1≤k≤l-1) except for the last one in the i-th pixel in the r-th divided viewing field.

Figure 5:
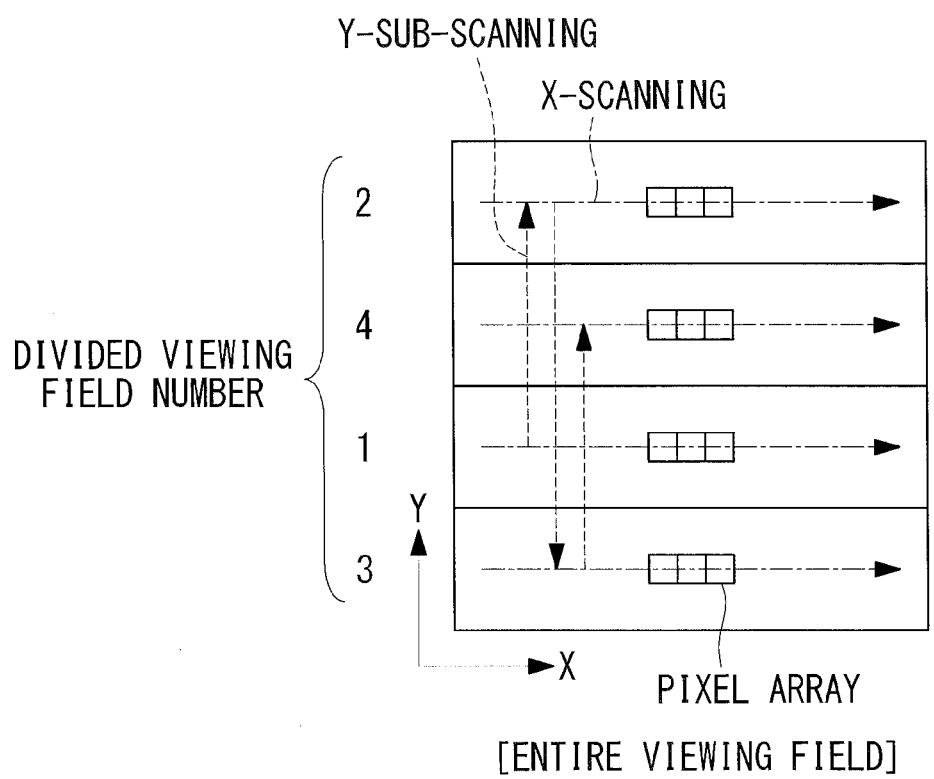
FIG. 5 is a diagram showing a modification of FIG. 4.

Regarding the scanning order of the divided viewing fields, although it has been assumed that they are scanned in a sequence in which they are switched in one direction in the example shown in FIG. 4, instead of this, they may be scanned by switching the divided viewing fields in any order as determined by the configuration of the scanning unit, for example, like the order shown in FIG. 5.

In addition, although it has been assumed that, in Math 2, the fluorescence intensity of each pixel is calculated by adding the detected fluorescence intensities after they have been corrected, instead of this, as shown in Math 3, the fluorescence intensities detected in each pixel may be corrected after being added.

$$SO_{iq} \quad \{\text{MATH 6}\}$$

$$\begin{cases} = \sum_{k=1}^{l} \left( SD_{ikq} - \exp(-\Delta t/T) \cdot \sum_{k=1}^{l} SD_{ik(q-1)} \right) \\ = SD_{iq} - \exp(-\Delta t/T) \cdot SD_{i(q-1)} & (2 \leq q \leq r) \\ \doteq SD_{i1} - \exp(-\Delta t/T) \cdot (l^{-1} SD_{(i-1)r} + (l-1)l^{-1} SD_{ir}) & (q=1) \end{cases}$$

The following aspect of invention is derived from the embodiment and modifications thereof described above.

One aspect of the present invention is a scanning observation apparatus including a scanning unit that spatially scans pulsed excitation light emitted from a light source at prescribed time intervals on a specimen; a fluorescence detecting unit that detects fluorescence generated by exciting a fluorescent substance inside the specimen with the excitation light scanned by the scanning unit, in synchronization with the emission of the excitation light; and a fluorescence correcting unit that subtracts, from a fluorescence intensity detected by the fluorescence detecting unit, an afterimage fluorescence component calculated on the basis of time-sequential fluorescence detected by the fluorescence detecting unit prior thereto, at each scanning position, to correct the fluorescence intensity at the scanning position.

With this aspect, the total fluorescence signal detected at an arbitrary time is corrected by calculating the afterimage fluorescence component included therein on the basis of the fluorescence signal prior to that time in the time sequence and subtracting this. Accordingly, it is possible to obtain the fluorescence signal generated at that time with good precision, and it is thus possible to obtain a high-resolution fluorescence image in which an afterimage is suppressed, even when the fluorescence detection interval is shortened.

In the above-described aspect, the fluorescence correcting unit may correct the fluorescence intensity on the basis of the following equations:

$$S_O = L^{-1} \cdot S_D$$

$$S_D = \begin{pmatrix} SD_1 \\ SD_2 \\ SD_3 \\ \vdots \\ SD_n \end{pmatrix} \quad \{\text{MATH 1}\}$$

$$L = \begin{pmatrix} l_{11} & l_{12} & l_{13} & \cdots & l_{1n} \\ l_{21} & l_{22} & l_{23} & \cdots & l_{2n} \\ l_{31} & l_{32} & l_{33} & \cdots & l_{3n} \\ \vdots & \vdots & \vdots & & \vdots \\ l_{n1} & l_{n2} & l_{n3} & \cdots & l_{nn} \end{pmatrix}$$

$$S_O = \begin{pmatrix} SO_1 \\ SO_2 \\ SO_3 \\ \vdots \\ SO_n \end{pmatrix}$$

where $S_O$ is a corrected fluorescence intensity, $SO_m$ is an m-th corrected fluorescence intensity, $S_D$ is a detected fluorescence intensity, $SD_m$ is an m-th detected fluorescence intensity, $\Delta t$ is the time interval of the excitation light, Tm is the fluorescence lifetime of a fluorescent dye, corresponding to the m-th detection, L is a fluorescence lifetime matrix, $l_{ij}=0 (i<j)$, and $lij=\exp(((j-i)\cdot\Delta t)/T_j)(\geq j)$.

By doing so, even in a case where the fluorescence lifetime is not spatially uniform, on the basis of the total of a plurality of fluorescence signals detected prior to the fluorescence detected at an arbitrary time and the fluorescence lifetime of each fluorescent dye corresponding to a plurality of detections prior to that time, it is possible to obtain the precisely-corrected fluorescence intensity at that time.

In the above-described aspect, the fluorescence correcting unit may correct the fluorescence intensity on the basis of the following equations:

$$SO_m = SD_m - SR_m$$

$$SR_m = \exp(-\Delta t/T) \cdot SD_{m-1}$$

where $SO_m$ is the m-th corrected fluorescence intensity, $SD_m$ is the m-th detected fluorescence intensity, $SR_m$ is the m-th afterimage component, $\Delta t$ is the time interval of the excitation light, and T is the fluorescence lifetime of the fluorescent dye.

By doing so, in the case where the fluorescence lifetime is spatially uniform, on the basis of the total of a plurality of fluorescence signals detected immediately prior to the fluorescence detected at an arbitrary time and the fluorescence lifetime of each dye corresponding to the detection immediately prior to that time, it is possible to obtain the fluorescence intensity at that time, which is easily and precisely corrected.

In the above-described aspect, each pixel may be formed of fluorescence generated by irradiation with pulsed excitation light a plurality of times; each scanning line may be formed of a plurality of the pixels; one viewing field may be formed of a plurality of divided viewing fields that are formed of a plurality of the scanning lines; and in the case where, for each irradiation with pulsed excitation light one time, the divided viewing field serving as an irradiation target is switched in a prescribed order, the fluorescence correcting unit may correct the fluorescence intensity on the basis of the following equation:

$$SO_{iq} = \sum_{k=1}^{l} SO_{ikq} \quad \{MATH\ 2\}$$

$$\begin{cases} = \sum_{k=1}^{l} (SD_{ikq} - \exp(-\Delta t/T) \cdot SD_{ik(q-1)}) & (2 \leq q \leq r) \\ = \sum_{k=1}^{l} SD_{ik1} - \exp(-\Delta t/T) \cdot \left(SD_{(i-1)lr} + \sum_{k=1}^{l-1} SD_{ikr}\right) & (q=1) \end{cases}$$

where l is the number of detections of the fluorescences forming each pixel, r is the total number of divided viewing fields, $SO_{iq}$ is the corrected fluorescence intensity in the i-th pixel in the q-th divided viewing field, $SO_{ikq}$ is the corrected fluorescence intensity, due to the k-th pulsed excitation light irradiation, in the i-th pixel in the q-th divided viewing field, $SD_{ikq}$ is the detected fluorescence intensity, due to the k-th pulsed excitation light irradiation, in the i-th pixel in the q-th divided viewing field, $SD_{ik1}$ is the detected fluorescence intensity, due to the k-th pulsed excitation light irradiation, in the i-th pixel in the first (initial) divided viewing field, and $SD_{(i-1)lr}$ is the detected fluorescence intensity, due to the l-th (final) pulsed excitation light irradiation, in the (i−1)-th pixel in the r-th (final) divided viewing field.

By doing so, in a case where the fluorescence lifetime is spatially uniform, a single viewing field is formed of a plurality of divided viewing fields which are switched in a prescribed order for each irradiation with the pulsed excitation light one time, and even in the case where fluorescence detection is performed multiple time in a single pixel, it is possible to obtain the fluorescence intensity at each time, which is easily and precisely corrected.

In the above-described aspect, each pixel may be formed of fluorescence generated by irradiation with pulsed excitation light a plurality of times; each scanning line may be formed of a plurality of the pixels; one viewing field may be formed of a plurality of divided viewing fields formed of a plurality of the scanning lines; and in the case where, for each irradiation with pulsed excitation light one time, the divided viewing field serving as an irradiation target is switched in a prescribed order, the fluorescence correcting unit may correct the fluorescence intensity on the basis of the following equation:

$$SO_{iq} \quad \{MATH\ 3\}$$

$$\begin{cases} = \sum_{k=1}^{l} \left(SD_{ikq} - \exp(-\Delta t/T) \cdot \sum_{k=1}^{l} SD_{ik(q-1)}\right) \\ = SD_{iq} - \exp(-\Delta t/T) \cdot SD_{i(q-1)} & (2 \leq q \leq r) \\ \phantom{=} SD_{i1} - \exp(-\Delta t/T) \cdot \\ \phantom{==} (l^{-1}SD_{(i-1)r} + (l-1)l^{-1}SD_{ir}) & (q=1) \end{cases}$$

where l is the number of detections of the fluorescences forming each pixel, r is the total number of divided viewing fields, $SO_{iq}$ is the corrected fluorescence intensity in the i-th pixel in the q-th divided viewing field, $SO_{ikq}$ is the corrected fluorescence intensity, due to the k-th pulsed excitation light irradiation, in the i-th pixel in the q-th divided viewing field, $SD_{iq}$ is the detected fluorescence intensity in the i-th pixel in the q-th divided viewing field, $SD_{i1}$ is the detected fluorescence intensity in the i-th pixel in the first (initial) divided viewing field, and $SD_{ir}$ is the detected fluorescence intensity in the i-th pixel in the r-th (final) divided viewing field.

By doing so, it is possible to obtain a high-resolution fluorescence image by adding all of the fluorescence detected in each pixel and then correcting them.

The present invention affords an advantage in that it is possible to obtain a high-resolution fluorescence image in which an afterimage is suppressed, even when the fluorescence detection interval is shortened.

REFERENCE SIGNS LIST

A specimen
1 scanning observation apparatus
2 light source
3 scanning unit
4 fluorescence detecting unit
5 fluorescence correcting unit

The invention claimed is:
1. A scanning observation apparatus comprising:
a scanning unit that spatially scans pulsed excitation light emitted from a light source at prescribed time intervals on a specimen;
a fluorescence detecting unit that detects fluorescence generated by exciting a fluorescent substance inside the specimen with the excitation light scanned by the scanning unit, in synchronization with the emission of the excitation light; and
a fluorescence correcting unit that subtracts, from a fluorescence intensity detected by the fluorescence detecting unit, an afterimage fluorescence component calculated on the basis of time-sequential fluorescence detected by the fluorescence detecting unit prior thereto, at each scanning position, to correct the fluorescence intensity at the scanning position,
wherein the fluorescence correcting unit corrects the fluorescence intensity on the basis of the following equations:

$$S_O = L^{-1} \cdot S_D$$

$$S_D = \begin{pmatrix} SD_1 \\ SD_2 \\ SD_3 \\ \vdots \\ SD_n \end{pmatrix} \quad \{\text{MATH 1}\}$$

$$L = \begin{pmatrix} l_{11} & l_{12} & l_{13} & \ldots & l_{1n} \\ l_{21} & l_{22} & l_{23} & \ldots & l_{2n} \\ l_{31} & l_{32} & l_{33} & \ldots & l_{3n} \\ \vdots & \vdots & \vdots & & \vdots \\ l_{n1} & l_{n2} & l_{n3} & \ldots & l_{nn} \end{pmatrix}$$

$$S_O = \begin{pmatrix} SO_1 \\ SO_2 \\ SO_3 \\ \vdots \\ SO_n \end{pmatrix}$$

where
$S_O$ is a corrected fluorescence intensity,
$SO_m$ is an m-th corrected fluorescence intensity,
$S_D$ is a detected fluorescence intensity,
$SD_m$ is an m-th detected fluorescence intensity,
$\Delta t$ is the time interval of the excitation light,
Tm is the fluorescence lifetime of a fluorescent dye, corresponding to the m-th detection,
L is a fluorescence lifetime matrix,
$l_{ij}=0$ (i<j), and
$l_{ij}=\exp(((j-i) \cdot \Delta t / T_j))$ (i≥j).

2. The scanning observation apparatus according to claim 1, wherein the fluorescence correcting unit corrects the fluorescence intensity on the basis of the following equations:

$$SO_m = SD_m - SR_m$$

$$SR_m = \exp(-\Delta t / T) \cdot SD_{m-1}$$

where
$SO_m$ is the m-th corrected fluorescence intensity,
$SD_m$ is the m-th detected fluorescence intensity,
$SR_m$ is the m-th afterimage component,
$\Delta t$ is the time interval of the excitation light, and
T is the fluorescence lifetime of the fluorescent dye.

3. The scanning observation apparatus according to claim 2:
each pixel is formed of fluorescences generated by irradiation with pulsed excitation light a plurality of times;
each scanning line is formed of a plurality of the pixels;
one viewing field is formed of a plurality of divided viewing fields that are formed of a plurality of the scanning lines; and
in the case where, for each irradiation with pulsed excitation light one time, the divided viewing field serving as an irradiation target is switched in a prescribed order, the fluorescence correcting unit corrects the fluorescence intensity on the basis of the following equation:

$$SO_{iq} = \sum_{k=1}^{l} SO_{ikq}$$

$$\begin{cases} = \sum_{k=1}^{l}(SD_{ikq} - \exp(-\Delta t/T) \cdot SD_{ik(q-1)}) & (2 \le q \le r) \\ = \sum_{k=1}^{l} SD_{ik1} - \exp(-\Delta t/T) \cdot \left( SD_{(i-1)|r} + \sum_{k=1}^{l-1} SD_{ikr} \right) & (q=1) \end{cases}$$

where
l is the number of detections of the fluorescences forming each pixel,
r is the total number of divided viewing fields,
$SO_{iq}$ is the corrected fluorescence intensity in the i-th pixel in the q-th divided viewing field,
$SO_{ikq}$ is the corrected fluorescence intensity, due to the k-th pulsed excitation light irradiation, in the i-th pixel in the q-th divided viewing field,
$SD_{ikq}$ is the detected fluorescence intensity, due to the k-th pulsed excitation light irradiation, in the i-th pixel in the q-th divided viewing field,
$SD_{ikq}$ is the detected fluorescence intensity, due to the k-th pulsed excitation light irradiation, in the i-th pixel in the first (initial) divided viewing field, and
$SD_{(i-1)|r}$ is the detected fluorescence intensity, due to the l-th (final) pulsed excitation light irradiation, in the (i−1)-th pixel in the r-th (final) divided viewing field.

4. The scanning observation apparatus according to claim 2, wherein:
each pixel is formed of fluorescences generated by irradiation with pulsed excitation light a plurality of times;
each scanning line is formed of a plurality of the pixels;
one viewing field is formed of a plurality of divided viewing fields formed of a plurality of the scanning lines; and in the case where, for each irradiation with pulsed excitation light one time, the divided viewing field serving as an irradiation target is switched in a prescribed order, the fluorescence correcting unit corrects the fluorescence intensity on the basis of the following equation:

$$SO_{iq} \begin{cases} = \sum_{k=1}^{l}\left(SD_{ikq} - \exp(-\Delta t/T) \cdot \sum_{k=1}^{l} SD_{ik(q-1)}\right) \\ = SD_{iq} - \exp(-\Delta t/T) \cdot SD_{i(q-1)} & (2 \le q \le r) \\ \doteq \dfrac{SD_{i1} - \exp(-\Delta t/T) \cdot}{(l^{-1}SD_{(i-1)r} + (l-1)l^{-1}SD_{ir})} & (q = 1) \end{cases}$$

where $l$ is the number of detections of the fluorescences forming each pixel, $r$ is the total number of divided viewing fields, $SO_{iq}$ is the corrected fluorescence intensity in the i-th pixel in the q-th divided viewing field, $SO_{ikq}$ is the corrected fluorescence intensity, due to the k-th pulsed excitation light irradiation, in the i-th pixel in the q-th divided viewing field, $SD_{iq}$ is the detected fluorescence intensity in the i-th pixel in the q-th divided viewing field, $SD_{i1}$ is the detected fluorescence intensity in the i-th pixel in the first (initial) divided viewing field, and $SD_{ir}$ is the detected fluorescence intensity in the i-th pixel in the r-th (final) divided viewing field.

\* \* \* \* \*